(12) United States Patent
Fields

(10) Patent No.: US 9,145,437 B2
(45) Date of Patent: Sep. 29, 2015

(54) UREA COMPOUNDS

(71) Applicant: Eli Lilly and Company, Indianapolis, IN (US)

(72) Inventor: Todd Fields, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/525,237

(22) Filed: Oct. 28, 2014

(65) Prior Publication Data

US 2015/0126469 A1    May 7, 2015

Related U.S. Application Data

(60) Provisional application No. 61/898,494, filed on Nov. 1, 2013.

(51) Int. Cl.
  *C07H 19/044* (2006.01)
  *C07H 19/06* (2006.01)
  *A61K 31/7042* (2006.01)
  *C07H 19/04* (2006.01)

(52) U.S. Cl.
  CPC ............ *C07H 19/06* (2013.01); *A61K 31/7042* (2013.01); *C07H 19/04* (2013.01); *C07H 19/044* (2013.01)

(58) Field of Classification Search
  None
  See application file for complete search history.

(56) References Cited

U.S. PATENT DOCUMENTS

| 7,750,145 | B2 | 7/2010 | Yonekubo et al. | |
| 7,851,617 | B2 | 12/2010 | Nomura et al. | |
| 8,697,849 | B2 | 4/2014 | Qu et al. | |
| 8,785,404 | B2 * | 7/2014 | Qu .................................. | 514/27 |
| 2008/0139484 | A1 | 6/2008 | Teranishi et al. | |

FOREIGN PATENT DOCUMENTS

| EP | 1803729 | * | 4/2007 |
| EP | 1803729 | A1 | 7/2007 |

OTHER PUBLICATIONS

U.S. Appl. No. 14/511,201, filed Oct. 10, 2014, Eli Lilly and Company.
International Search Report, PCT/US2014/060882, Nov. 26, 2014, Eli Lilly and Company.
Written Opinion of the International Searching Authority, PCT/US2014/060882, Nov. 26, 2014, Eli Lilly and Company.

* cited by examiner

*Primary Examiner* — Traviss C McIntosh, III
(74) *Attorney, Agent, or Firm* — Nelsen L. Lentz

(57) ABSTRACT

The present invention provides a compound of Formula I:

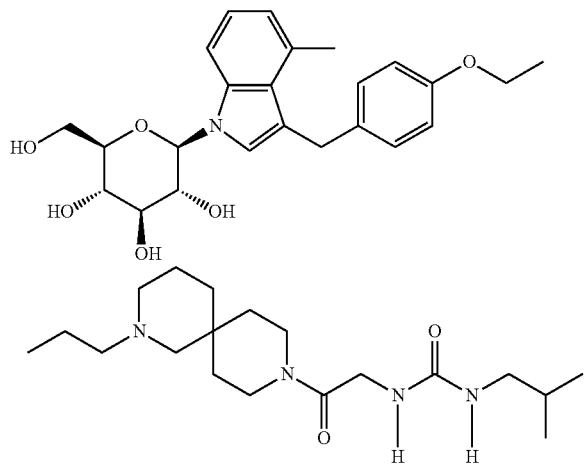

Formula I or a pharmaceutically acceptable salt thereof.

6 Claims, No Drawings

UREA COMPOUNDS

The present invention relates to novel urea compounds, to pharmaceutical compositions comprising the compounds, to methods of using the compounds to treat physiological disorders, and to intermediates and processes useful in the synthesis of the compounds.

The present invention is in the field of treatment of diabetes and other diseases and disorders associated with hyperglycemia. Diabetes is a group of diseases that is characterized by high levels of blood glucose. It affects approximately 25 million people in the United States and is also the 7$^{th}$ leading cause of death in U.S. according to the 2011 National Diabetes Fact Sheet (U.S. Department of Health and Human Services, Centers for Disease Control and Prevention). Sodium-coupled glucose cotransporters (SGLT's) are one of the transporters known to be responsible for the absorption of carbohydrates, such as glucose. More specifically, SGLT1 is responsible for the transport of glucose across the brush border membrane of the small intestine Inhibition of SGLT1 may result in reduced absorption of glucose in the small intestine, thus providing a useful approach to treating diabetes.

U.S. Patent Application Publication No. 2008/0139484 A1 discloses 1-(β-D-glycopyranosyl)-3-substituted nitrogen-containing heterocyclic compounds having SGLT1 and/or SGLT2 inhibitory activity which are further disclosed as being useful for the prevention or treatment of a disease associated with hyperglycemia, such as diabetes. In addition, U.S. Pat. No. 7,851,617 discloses indole deriviatives which are SGLT inhibitors and are further disclosed as being useful for treatment or prevention of diabetes and related conditions.

There is a need for alternative drugs and treatment for diabetes. The present invention provides certain novel inhibitors of SGLT1 which may be suitable for the treatment of diabetes.

Accordingly, the present invention provides a compound of Formula I:

glucose (IFG), or metabolic syndrome in a patient comprising administering to a patient in need of such treatment an effective amount of a compound of Formula I, or a pharmaceutically acceptable salt thereof.

Furthermore, this invention provides a compound of Formula I or a pharmaceutically acceptable salt thereof for use in therapy, in particular for the treatment of diabetes. In addition, this invention provides a compound of Formula I or a pharmaceutically acceptable salt thereof for use in the treatment of type 1 diabetes. In addition, this invention provides a compound of Formula I or a pharmaceutically acceptable salt thereof for use in the treatment of type 2 diabetes. The invention further provides a compound of Formula I or a pharmaceutically acceptable salt thereof for use in the treatment of impaired glucose tolerance (IGT), impaired fasting glucose (IFG), or metabolic syndrome. This invention also provides the use of a compound of Formula I, or a pharmaceutically acceptable salt thereof, for the manufacture of a medicament for the treatment of diabetes. Furthermore, this invention provides the use of a compound of Formula I, or a pharmaceutically acceptable salt thereof, for the manufacture of a medicament for the treatment of type 1 diabetes. This invention also provides the use of a compound of Formula I, or a pharmaceutically acceptable salt thereof, for the manufacture of a medicament for the treatment of type 2 diabetes. The invention also provides the use of a compound of Formula I, or a pharmaceutically acceptable salt thereof, for the manufacture of a medicament for the treatment of IGT, IFG, or metabolic syndrome.

The invention further provides a pharmaceutical composition comprising a compound of Formula I, or a pharmaceutically acceptable salt thereof, with one or more pharmaceutically acceptable carriers, diluents, or excipients. This invention also encompasses novel intermediates and processes for the synthesis of the compound of Formula I.

As used herein, the terms "treating" or "to treat" includes restraining, slowing, stopping, or reversing the progression or severity of an existing symptom or disorder.

Formula I

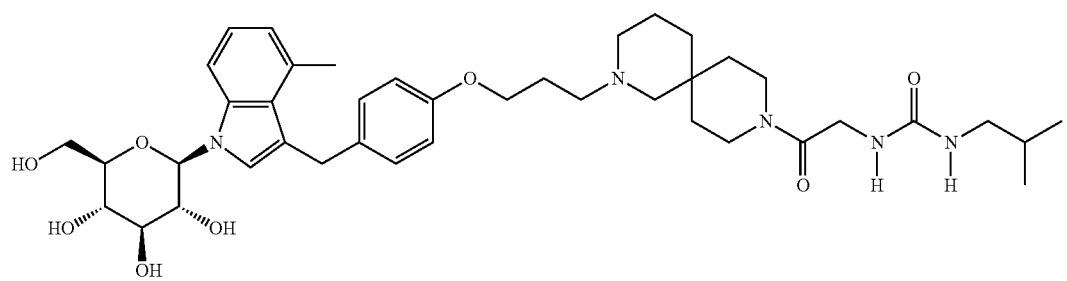

or a pharmaceutically acceptable salt thereof.

The present invention also provides a method of treating diabetes in a patient comprising administering to a patient in need of such treatment an effective amount of a compound of Formula I, or a pharmaceutically acceptable salt thereof. The present invention further provides a method of treating type 1 diabetes in a patient comprising administering to a patient in need of such treatment an effective amount of a compound of Formula I, or a pharmaceutically acceptable salt thereof. In addition, the present invention provides a method of treating type 2 diabetes in a patient comprising administering to a patient in need of such treatment an effective amount of a compound of Formula I, or a pharmaceutically acceptable salt thereof. The present invention also provides a method of treating impaired glucose tolerance (IGT), impaired fasting As used herein, the term "patient" refers to a mammal, such as a mouse, guinea pig, rat, dog, or human. It is understood that the preferred patient is a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of Formula I are generally effective over a wide dosage range. For example, dosages per day normally fall within the range of about 0.01 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way.

The compounds of the invention are preferably formulated as pharmaceutical compositions administered by any route which makes the compound bioavailable. Most preferably, such compositions are for oral administration. Such pharmaceutical compositions and processes for preparing same are well known in the art. (See, e.g., Remington: The Science and Practice of Pharmacy (D. B. Troy, Editor, 21st Edition., Lippincott, Williams & Wilkins, 2006).

In a further aspect of the invention, the present compounds are administered in combination with one or more therapeutic agents, such as antidiabetic agents. Administration in combination includes simultaneous or sequential administration. In addition, simultaneous administration of the combination can be as a single combination dose or separate doses of each therapeutic agent. Examples of antidiabetic agents include metformin; a DPPIV inhibitor, such as sitagliptin or linagliptin; a sulfonylurea, such as glimepiride; a thiazolidinedione, such as pioglitazone; a basal insulin, such as glargine; a rapid acting insulin, such as HUMALOG or NOVOLOG; a GLP-1 agonist, such as exenatide or liraglutide; an SGLT2 inhibitor, such as dapagliflozin or empagliflozin; a glucagon receptor antagonist, such as LY2409021; and the like.

Compounds of Formula I are prepared as illustrated in the preparations, examples, and schemes below. The reagents and starting materials are readily available to one of ordinary skill in the art. All substituents, unless otherwise specified are as previously defined. It is understood that these schemes, preparations, and examples are not intended to be limiting to the scope of the invention in any way.

Examples of resolutions include selective crystallization techniques or chiral chromatography. (See, e.g. J. Jacques, et al., "Enantiomers, Racemates, and Resolutions", John Wiley and Sons, Inc., 1981, and E. L. Eliel and S. H. Wilen," Stereochemistry of Organic Compounds", Wiley-Interscience, 1994). It should be further clear to one of ordinary skill in the art that separation and isolation, by chromatography, chiral chromatography or selective crystallization, of individual diastereomers or geometric isomers of Formula I or individual diastereomers or geometric isomers of intermediates leading to Formula I, can occur at any convenient point in the synthesis.

As used herein, "δ" refers to parts per million down-field from tetramethylsilane; "mins" refers to minute or minutes; "hrs" refers to hours; "THF" refers to tetrahydrofuran; "EtOAc" refers to ethyl acetate; "MeOH" refers to methanol or methyl alcohol; "EtOH" refers to ethanol or ethyl alcohol; "TFA" refers to trifluoroacetic acid; "DPPA" refers to diphenylphosphoryl azide; "HATU" refers to O-(7-azabenzotriazol-1-yl)-N,N,N',N'tetramethyluronium hexafluorophosphate; "CDI" refers to 1,1'-carbonyldiimidazole; "DDQ" refers to 2,3-dichloro-5,6-dicyano-1,4-benzoquinone "Xphos" refers to 2-dicyclohexylphosphino-2',4',6'-triisopropylbiphenyl; "MTBE" refers to methyltert-butylether; "HPLC" refers to high-performance liquid chromatography; "Ac" refers to an acetyl substituent of the following structure:

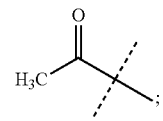

and the term "BOC" refers to a t-butyloxycarbonyl protecting group.

Pharmaceutically acceptable salts and common methodology for preparing them are well known in the art. See, e.g., Gould, P. L., "Salt selection for basic drugs," *International Journal of Pharmaceutics,* 33:201-217 (1986); Bastin et al. "Salt Selection and Optimization Procedures for Pharmaceutical New Chemical Entities," *Organic Process Research and Development,* 4:427-435 (2000); and S. M. Berge, et al., "Pharmaceutical Salts," Journal of Pharmaceutical Sciences, Vol. 66, No. 1, January 1977. One skilled in the art of synthesis will appreciate that the compounds of Formula I as amines are organic bases, and that they are readily converted to and isolated as pharmaceutically acceptable salts using techniques and conditions well known to one of ordinary skill in the art.

Scheme I

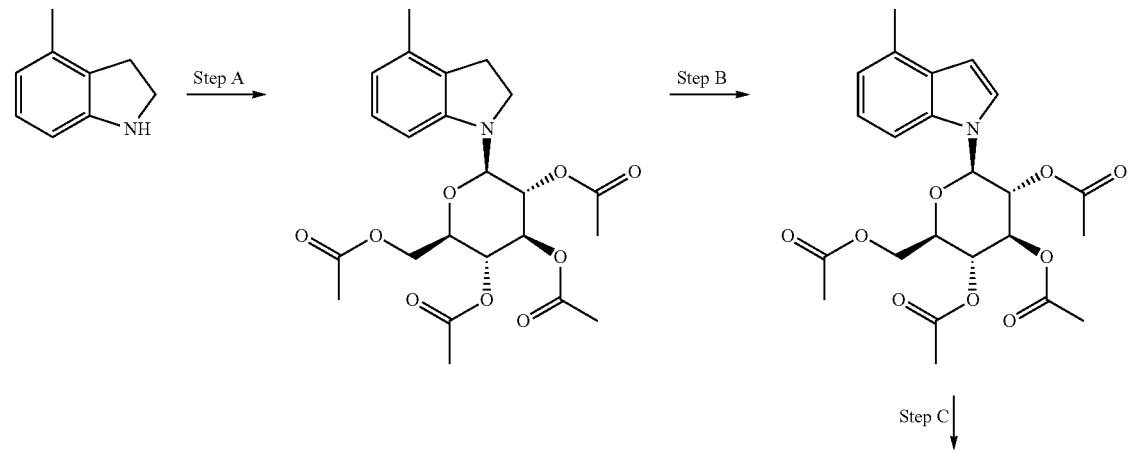

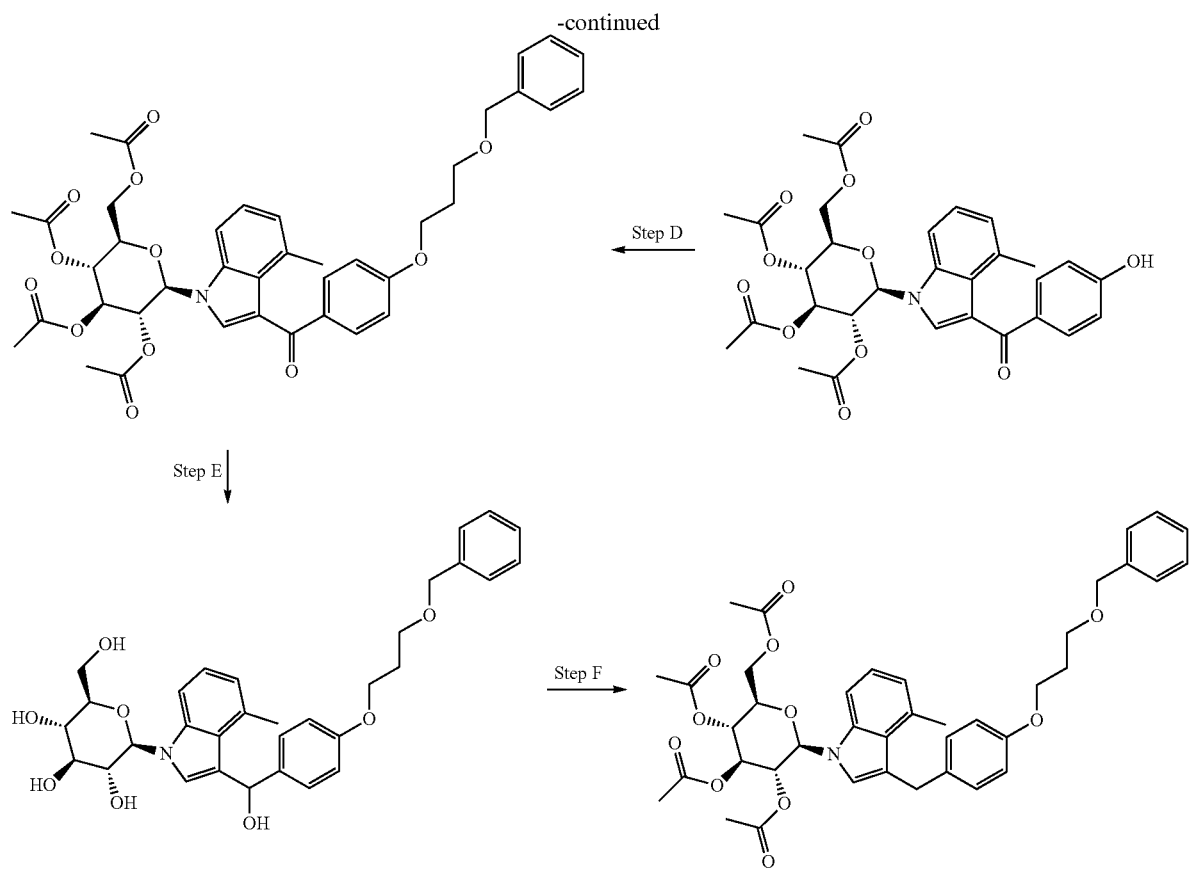

PREPARATION 1

4-methylindoline

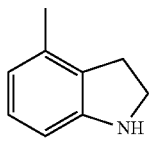

Method A

Charge 4-methyl-1H-indole (500 g; 1.0 equiv; 3.811 moles) and acetic acid (2000 mL) to a 20 L flask at room temperature. Cool the solution to 0° C. (internal temperature) and then add sodium cyanoborohydride (359.2 g; 1.5 equiv; 5.71 moles) in 5 equal portions, while not allowing the reaction mixture to warm above 10° C. When the addition is complete, stir the reaction mixture at room temperature for 2 hours. Cool the reaction mixture to 0° C. and add ice (5 Kg). Add a pre-cooled (5° C.) solution of sodium hydroxide (4M) very slowly to achieve a reaction mixture pH of 14. Extract the reaction mixture with ethyl acetate (2×10 L). Combine the organic layers and wash with water (1×10 L) and brine (1×10 L). Dry over anhydrous sodium sulfate, filter, and concentrate under reduced pressure to obtain the title compound (460 g, 90% yield): mass spectrum (m/z):134 (M+1).

Method B

Charge trifluoroacetic acid (7.62 moles; 576.42 mL) to a 2000 mL 3 necked flask, equipped with thermometer, magnetic stirrer, nitrogen line, and dropping funnel. Place the flask in an ice/water bath and cool the mixture to 13° C. (internal temperature). Add 4-methyl-1H-indole (762.33 mmoles; 94.25 mL; 100.00 g) over 3 minutes not allowing the temperature of the reaction mixture to exceed 25° C. Stir the mixture for about 1 minute after the addition is complete, allowing the temperature of the reaction mixture to reach 20° C., then remove the flask from the ice bath and stir for 10 minutes at 20° C. Add triethylsilane (876.68 mmoles; 140.47 mL; 101.94 g) dropwise to the reaction over 41 minutes, allowing the temperature to rise to 25° C., then maintaining the temperature between 25° C. and 30° C. by use of a cool water bath as required. When the addition is complete stir the reaction mixture for 80 minutes. Cool the reaction mixture to 10° C. then pour into a mixture of ice (1000 g) 5 M hydrochloric acid (800 ml) and MTBE (2000 ml) with stirring. Note that it is important to quench into a biphasic system to prevent the formation of impurities. Separate the aqueous phase and extract the organics with hydrochloric acid (400 ml; 2 M), then hydrochloric acid (2×200 ml; 2 M). Combine the aqueous extracts and cool in ice water. Add 50% w/w NaOH to achieve pH>10 keeping the temperature below 30° C. Extract the aqueous mixture with MTBE (1000 ml, then 200 ml). Combine the organic extracts, dry over anhydrous sodium sulfate, filter, and concentrate under reduced pressure to give the title compound (73 g; 68% yield): mass spectrum (m/z): 134 (M+1).

Method C

Add a solution of 4-methyl-1H-indole, (114.35 mmoles; 15.00 g) in tetrahydrofuran (75.00 mL) to a solution of p-toluenesulfonic acid monohydrate (137.22 mmoles; 23.63 g) in water (75.00 mL) with stirring at room temperature. Add 5% platinum on carbon (Johnson Matthey Type 103; 1.50 g) under a blanket of carbon dioxide. Place the mixture under an atmosphere of hydrogen (4.2 bar) and shake at room temperature overnight. Dilute the reaction mixture with sodium hydroxide (2M aqueous solution; 148.65 mmoles; 74.33 mL) and stir with MTBE (150.00 mL). Filter the mix through diatomaceous earth and wash the pad with MTBE (50 mL). Separate the filtrate and extract the aqueous with MTBE (100 mL). Combine the organics, dry over anhydrous magnesium sulfate, filter, and concentrate under reduced pressure to give the title compound (14.80 g; 97.17% yield): mass spectrum (m/z): 134 (M+1).

PREPARATION 2

[(2R,3R,4S,5R,6R)-3,4,5-triacetoxy-6-(4-methylindolin-1-yl)tetrahydropyran-2-yl]methyl acetate

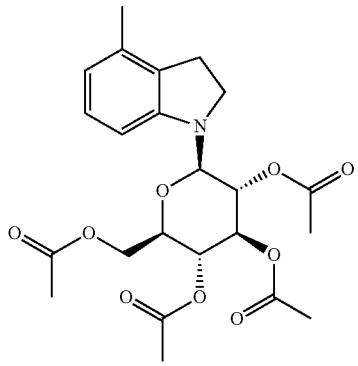 [SMILES: CC(=O)OC[C@H]1O[C@@H](N2CCc3c(C)cccc32)[C@H](OC(C)=O)[C@@H](OC(C)=O)[C@@H]1OC(C)=O]

Method A

Scheme I, Step A: Wet D-glucose (180.2 mmol) with water (25 mL) and then add 4-methylindoline, (180.2 mmoles) in ethanol (200 mL). Purge the mixture with nitrogen and heat to reflux under nitrogen atmosphere overnight. Then cool to room temperature and concentrate under reduced pressure. To the resulting residue, add dichloromethane (200 mL), N,N-dimethylaminopyridine (9.0 mmol), and pyridine (2.5 mol). Cool the mixture in an ice bath and then add acetic acid anhydride (1.1 mol) dropwise over 30 mins Concentrate the mixture under reduced pressure, dilute the residue with ethyl acetate (500 mL), and wash the mixture with citric acid (saturated aqueous solution; 50 mL) in water (500 mL). Wash with brine (500 mL), dry over sodium sulfate, filter, and concentrate under reduced pressure. Add ethanol (500 mL) and mix at 50° C. for 10 minutes. Cool the mixture to room temperature and then in ice/water. Filter the resulting mixture and dry under reduced pressure to give the title compound (32 g; 38.32% yield): mass spectrum (m/z): 464.2 (M+1).

Method B

Scheme I, Step A: Charge to a 20 L three neck flask a solution of 4-methylindoline (1000 g; 7.51 moles) in ethanol:water (8000 ml: 1000 ml) and D-glucose (1480 g; 8.25 moles). Heat the mixture for 6 hours at 80° C. Concentrate the mixture under reduced pressure and dissolve the residue in pyridine:dichloromethane (8000 ml:8000 ml). Add dimethylaminopyridine (91.79 g; 0.75 moles) and cool the reaction mixture to 10° C. (internal temperature). Add acetic anhydride (9000 ml) dropwise. When the addition is complete stir the reaction mixture for 1 hour at 45° C. and then stir overnight at room temperature. Concentrate the mixture under reduced pressure. Add ethyl acetate (20 L) and water (10 L) to the residue. Separate the organic layer and extract the aqueous layer with ethyl acetate (2×10 L). Combine the organic layers and wash with a saturated solution of citric acid (5 Kg) in water. Dry the organic layer over anhydrous sodium sulfate, filter, and concentrate under reduced pressure. Crystallise the residue from ethanol to give the title compound (3205.5 g; 92.11% yield): mass spectrum (m/z): 464.2 (M+1).

Method C

Scheme I, Step A: Wet D-glucose (517.30 mmoles; 93.20 g) with water (66 mL) and then add 4-methylindoline, (65.62 g; 492.67 mmoles) in ethanol (394 mL). Purge the mixture with nitrogen and heat to reflux under nitrogen atmosphere overnight. Then cool to room temperature and concentrate under reduced pressure. To the resulting residue, add dichloromethane (394 mL), triethylamine (2.82 moles; 393.72 mL), and N,N-dimethyl-4-pyridinamine, (24.63 mmoles; 3.01 g). Cool the mixture in an ice bath and then add acetic acid anhydride (3.94 moles; 372.57 mL) dropwise over 30 mins Concentrate the mixture under reduced pressure, dilute the residue with ethyl acetate (984 mL), and wash the mixture with citric acid (saturated aqueous solution; 50 mL) in water (200 mL). Separate the layers and extract the aqueous with ethyl acetate (600 mL then 300 mL). Combine the organics, wash with brine (600 mL), and concentrate under reduced pressure. Add ethanol (656 mL) and mix at 50° C. for 10 minutes. Cool the mixture to room temperature and then in ice/water. Filter the resulting mixture and dry under reduced pressure to give the title compound (112.2 g; 49.14% yield): mass spectrum (m/z): 464.2 (M+1).

PREPARATION 3

[(2R,3R,4S,5R,6R)-3,4,5-triacetoxy-6-(4-methylindol-1-yl)tetrahydropyran-2-yl]methyl acetate

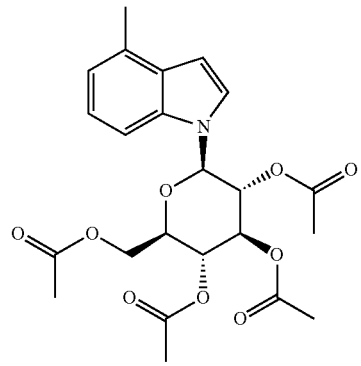 [SMILES: CC(=O)OC[C@H]1O[C@@H](n2ccc3c(C)cccc32)[C@H](OC(C)=O)[C@@H](OC(C)=O)[C@@H]1OC(C)=O]

Method A

Scheme I, Step B: Charge [(2R,3R,4S,5R,6R)-3,4,5-triacetoxy-6-(4-methylindolin-1-yl)tetrahydropyran-2-yl]methyl acetate (60.4 mmol) to a 500 mL flask. Add 1,4 dioxane (250 mL) and cool the solution to 10° C. Add DDQ (63.4 mmol) in one portion. Warm the mixture to room temperature and stir for 2 hours. Filter the reaction mixture and wash the solid with 1,4-dioxane (3×50 mL). Concentrate the filtrate under reduced pressure and filter through a plug of silica gel (200 g) rinsing with 10% EtOAc/dichloromethane (300 mL). Wash with a saturated solution of sodium bicarbonate (2×200 mL) then water (200 mL). Dry over anhydrous sodium sulphate, filter, concentrate under reduced pressure to give the title compound (27.5 g; 98.6% yield): mass spectrum (m/z): 462.5 (M+1).

Method B

Scheme I, Step B: Charge [(2R,3R,4S,5R,6R)-3,4,5-triacetoxy-6-(4-methylindolin-1-yl)tetrahydropyran-2-yl]methyl acetate (4200 g; 9.08 moles) to a 20 L flask. Add 1,4 dioxane (42000 mL) and cool the solution to 10° C. Add DDQ (2057 g; 9.08 moles) in 5 equal portions maintaining the temperature at 10° C. After addition is complete, warm the mixture to room temperature and stir for 2 hours. Filter the reaction mixture and wash the solid with 1,4-dioxane (3 times). Concentrate the filtrate under reduced pressure and purify the residue by column chromatography eluting with 0%-20% ethyl acetate in hexane. Combine pure fractions with a separate lot of material prepared in a similar manner starting from 2500 g of [(2R,3R,4S,5R,6R)-3,4,5-triacetoxy-6-(4-methylindolin-1-yl)tetrahydropyran-2-yl]methyl acetate and concentrate under reduced pressure. Dissolve the residue in ethyl acetate (50 L) and wash with a saturated solution of sodium bicarbonate (2×20 L) then water (1×10 L). Dry over anhydrous sodium sulphate, filter, concentrate under reduced pressure, and crystallize from ethanol (10 L) to give the title compound (4.632 Kg; 69% yield): mass spectrum (m/z): 462.5 (M+1).

Method C

Scheme I, Step B: Dissolve [(2R,3R,4S,5R,6R)-3,4,5-triacetoxy-6-(4-methylindolin-1-yl)tetrahydropyran-2-yl]methyl acetate (112.2 g; 242.08 mmoles) in 1,4-dioxane (1.68 L) at room temperature. Cool the mixture in an ice/water bath, then add 4,5-dichloro-3,6-dioxo-cyclohexa-1,4-diene-1,2-dicarbonitrile (244.50 mmoles; 55.50 g) portion-wise keeping the temperature of the reaction mixture below 15° C. When the addition is complete, stir the mixture for 5 minutes, then remove from the ice bath and stir for a further 5 minutes. Filter the mixture and wash the solid with 1,4-dioxane (561.00 mL). Concentrate the filtrate under reduced pressure, then add ethanol (561.00 mL) to the residue, and stir at 40° C. for 20 minutes. Cool the mixture in ice water for 15 mins, filter, and wash the solid obtained with cold ethanol (100 mL). Dry the solid under reduced pressure to give the title compound (82.5 g; 73.9% yield): mass spectrum (m/z): 462.0 (M+1).

PREPARATION 4

[(2R,3R,4S,5R,6R)-3,4,5-triacetoxy-6-[3-(4-hydroxybenzoyl)-4-methyl-indol-1-yl]tetrahydropyran-2-yl]methyl acetate

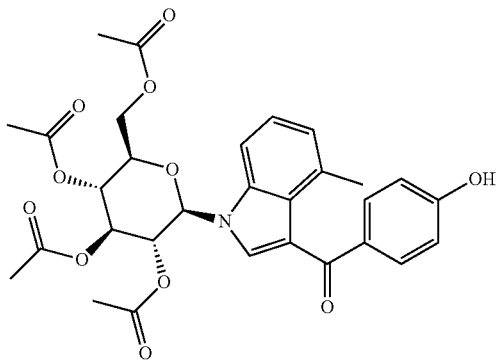 [SMILES: CC(=O)OC[C@H]1O[C@@H](n2cc(C(=O)c3ccc(O)cc3)c3c(C)cccc32)[C@H](OC(C)=O)[C@@H](OC(C)=O)[C@@H]1OC(C)=O]

Scheme I, Step C: To a 0.5 L stirred round bottom, purged with nitrogen, charge in order: [(2R,3R,4S,5R,6R)-3,4,5-triacetoxy-6-(4-methylindol-1-yl)tetrahydropyran-2-yl]methyl acetate (29.5 mmol), dichloromethane (100 mL), and 4-bromobenzoyl chloride (30.9 mmol). Cool the mixture in an icebath and add aluminum trichloride (88.4 mmol). After stirring, with cooling, for 1.5 hours, pour the reaction mixture over ice and dilute with water (100 mL) and chloroform (100 mL). Separate the organic phase and wash the aqueous with chloroform (100 mL). Combine the organics and wash with concentrated sodium bicarbonate solution (200 mL) and brine (200 mL). Dry over sodium sulphate, filter, and concentrate. Purify by flash chromatography over silica gel (330 g) eluting with 5-25% EtOAc/chloroform to give the title compound (7.9 g; 46.09% yield): mass spectrum (m/z): 582.4 (M+1), 580.4 (M−H).

PREPARATION 5

[(2R,3R,4S,5R,6R)-3,4,5-triacetoxy-6-[3-[4-(3-benzyloxypropoxy)benzoyl]-4-methyl-indol-1-yl]tetrahydropyran-2-yl]methyl acetate

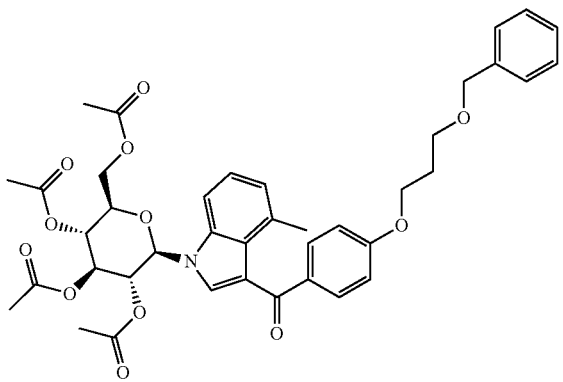 [SMILES: CC(=O)OC[C@H]1O[C@@H](n2cc(C(=O)c3ccc(OCCCOCc4ccccc4)cc3)c3c(C)cccc32)[C@H](OC(C)=O)[C@@H](OC(C)=O)[C@@H]1OC(C)=O]

Scheme I, Step D: To a 0.5 L stirred round bottom, purged with nitrogen, charge in order: [(2R,3R,4S,5R,6R)-3,4,5-triacetoxy-6-[3-(4-hydroxybenzoyl)-4-methyl-indol-1-yl]tetrahydropyran-2-yl]methyl acetate (13.58 mmol), acetonitrile (250 mL), and potassium carbonate (67.92 mmol). To this stirred solution, at room temperature, add 3-bromopropoxymethylbenzene (27.2 mmol) and heat at 60° C. for 16 hours under nitrogen. Dilute with EtOAc (200 mL) and filter. Concentrate the filtrate and purify by flash chromatography (330 g silica gel) eluting with 2-40% EtOAc/chloroform. Concentrate the product containing fractions to give the title compound (9.0 g. 90.79%): mass spectrum (m/z): 730.4 (M+H).

PREPARATION 6

(2R,3R,4S,5S,6R)-2-[3-[[4-(3-benzyloxypropoxy)phenyl]-hydroxy-methyl]-4-methyl-indol-1-yl]-6-(hydroxymethyl)tetrahydropyran-3,4,5-triol

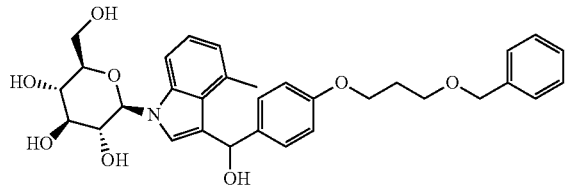 [SMILES: Cc1cccc2c1c(C(O)c1ccc(OCCCOCc3ccccc3)cc1)cn2[C@@H]1O[C@H](CO)[C@@H](O)[C@H](O)[C@H]1O]

Scheme I, Step E: To a 0.5 L stirred round bottom flask, purged with nitrogen, charge [(2R,3R,4S,5R,6R)-3,4,5-triacetoxy-6-[3-[4-(3-benzyloxypropoxy)benzoyl]-4-methyl-indol-1-yl]tetrahydropyran-2-yl]methyl acetate (12.33 mmol), THF (50 mL), and ethanol (100 mL). Add sodium tetrahydroborate (37.0 mmol) and stir at room temperature for 6 hours. Acidify by dropwise addition of 5N HCl then dilute with water (200 mL) and dichloromethane (200 mL). Separate the organics and wash with brine (200 mL). Dry over sodium sulphate, filter, and concentrate to give the title compound as a mixture of diastereomers in sufficient purity to be used without further purification in the next step (7.2 g crude) mass spectrum (m/z): 546.4 (M+1-18).

PREPARATION 7

[(2R,3R,4S,5R,6R)-3,4,5-triacetoxy-6-[3-[[4-(3-benzyloxypropoxy)phenyl]methyl]-4-methyl-indol-1-yl]tetrahydropyran-2-yl]methyl acetate

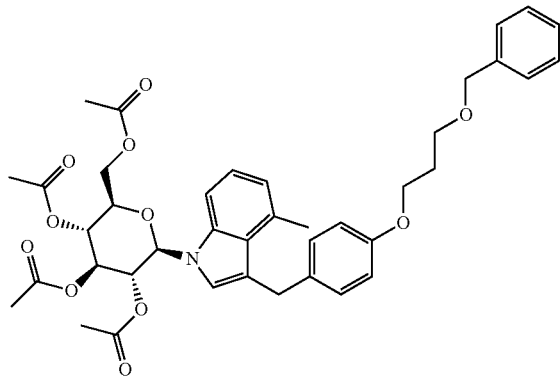 [SMILES: CC(=O)OC[C@H]1O[C@@H](n2cc(Cc3ccc(OCCCOCc4ccccc4)cc3)c3c(C)cccc32)[C@H](OC(C)=O)[C@@H](OC(C)=O)[C@@H]1OC(C)=O]

Scheme I, Step F: To a 0.5 L round bottom flask under nitrogen charge (2R,3R,4S,5S,6R)-2-[3-[[4-(3-benzyloxypropoxy)phenyl]-hydroxy-methyl]-4-methyl-indol-1-yl]-6-(hydroxymethyl)tetrahydropyran-3,4,5-triol (7.2 g. Crude), then acetonitrile (50 mL), and then dichloromethane (100 mL). Cool the mixture to 0° C. Add triethylsilane (63.87 mmol) followed by dropwise addition of boron trifluoride etherate (51.10 mmol). When the addition is complete stir the reaction mixture in the ice bath for 5 minutes then quench by dropwise addition of sodium bicarbonate solution (20 mL). Dilute with water (200 mL) and EtOAc (500 mL). Separate the layers, wash the organic phase with brine (200 mL), and concentrate under reduced pressure. Add pyridine (50 mL), dichloromethane (50 mL) and N,N-dimethylaminopyridine (0.41 mmol). Cool in an ice bath and add acetic anhydride (127.74 mmol). Warm to room temperature and stir for 16 hours. Concentrate under reduced pressure then add EtOAc (500 mL). Wash with a citric acid solution (200 mL) followed by water (200 mL) and brine (200 mL). Dry over sodium sulphate, filter, and concentrate. Purify by flash chromatography(330 g silica gel) eluting with 5 –5-20% EtOAc/dichloromethane to give the title compound (7.5 g, 82.03%): mass spectrum (m/z): 716.3 (M+1).

Scheme II

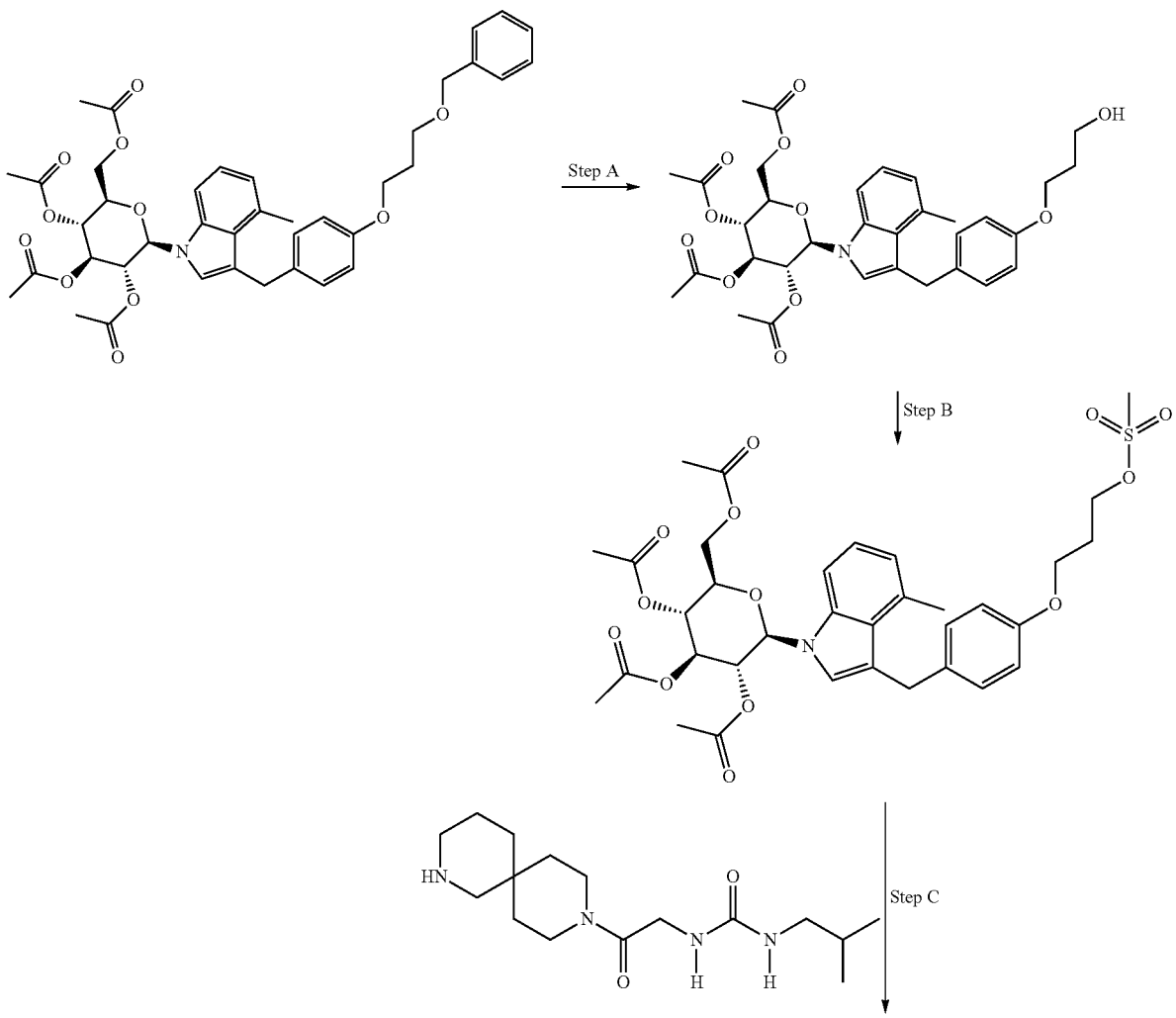

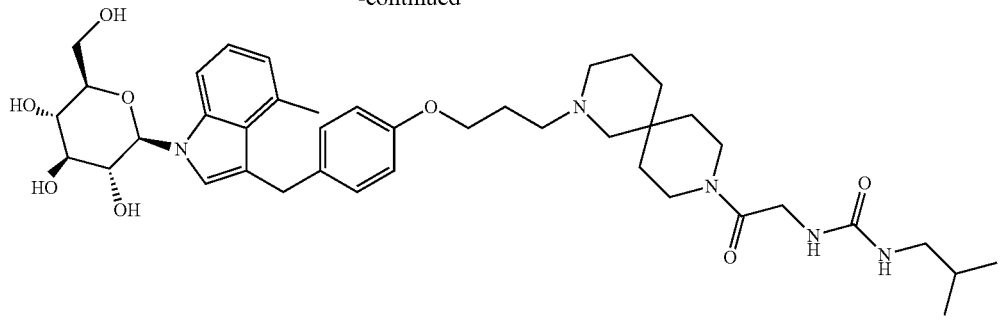

Formula I

PREPARATION 8

[(2R,3R,4S,5R,6R)-3,4,5-triacetoxy-6-[3-[[4-(3-hydroxypropoxy)phenyl]methyl]-4-methyl-indol-1-yl]tetrahydropyran-2-yl]methyl acetate

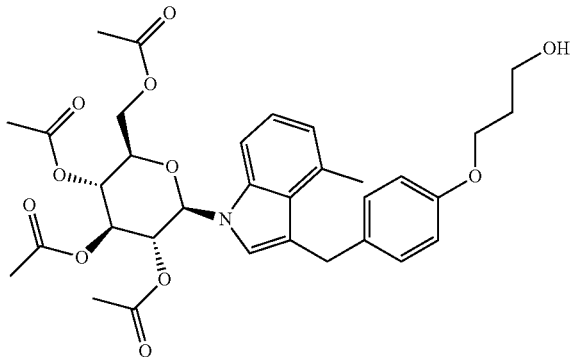 [SMILES: CC(=O)OC[C@H]1O[C@@H](n2cc(Cc3ccc(OCCCO)cc3)c3c(C)cccc32)[C@H](OC(C)=O)[C@@H](OC(C)=O)[C@@H]1OC(C)=O]

Scheme II, Step A: To a 0.5 L round bottom flask add [(2R,3R,4S,5R,6R)-3,4,5-triacetoxy-6-[3-[[4-(3-benzyloxypropoxy)phenyl]methyl]-4-methyl-indol-1-yl]tetrahydropyran-2-yl]methyl acetate (10.34 mmol) and ethyl acetate (80 mL). To this solution add 5% Pd/C pre wet with ethyl acetate (20 mL). While stirring, vacuum purge the mixture with hydrogen (3×) then stir under hydrogen for 16 hours. Filter through diatomaceous earth and rinse with ethyl acetate (100 mL). Concentrate the filtrate under reduced pressure to give the title compound in sufficient purity to use in the next step (6.5 g): mass spectrum (m/z): 626.4 (M+1).

PREPARATION 9

[(2R,3R,4S,5R,6R)-3,4,5-triacetoxy-6-[4-methyl-3-[[4-(3-methylsulfonyloxypropoxy)phenyl]methyl]indol-1-yl]tetrahydropyran-2-yl]methyl acetate

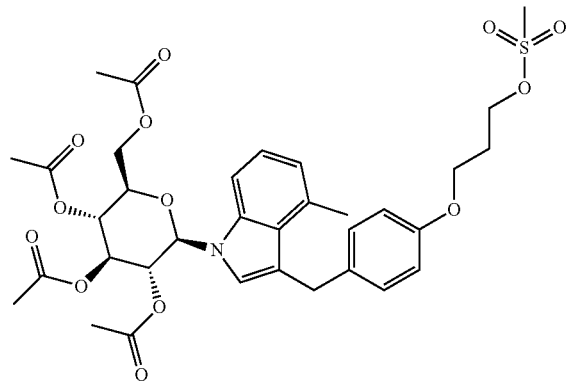 [SMILES: CC(=O)OC[C@H]1O[C@@H](n2cc(Cc3ccc(OCCCOS(C)(=O)=O)cc3)c3c(C)cccc32)[C@H](OC(C)=O)[C@@H](OC(C)=O)[C@@H]1OC(C)=O]

Scheme II, Step B: To a 0.5 L round bottom flask add [(2R,3R,4S,5R,6R)-3,4,5-triacetoxy-6-[3-[[4-(3-hydroxypropoxy)phenyl]methyl]-4-methyl-indo-1-yl]tetrahydropyran-2-yl]methyl acetate (6.5 g, crude), dichloromethane (100 mL), and triethylamine (25.97 mmol). Cool in an ice bath and add methanesulfonyl chloride (12.47 mmol) dropwise over 10 minutes. Warm to room temperature and stir for 1 hour. Dilute with dichloromethane (100 mL) and wash with water (200 mL) and brine (200 mL). Dry the organics over sodium sulfate, filter, and concentrate under vacuum to give the title compound in sufficient purity to use in the next step (7.2 g): mass spectrum (m/z): 704.4 (M+1).

PREPARATION 10a

1-[2-(4,9-diazaspiro[5.5]undecan-9-yl)-2-oxo-ethyl]-3-isobutyl-urea

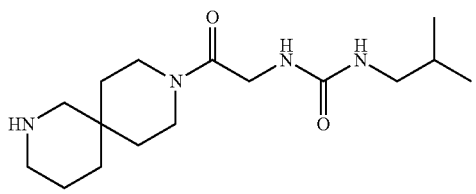 [SMILES: CC(C)CNC(=O)NCC(=O)N1CCC2(CCCNC2)CC1]

To a round bottom flask add tert-butyl 4,9-diazaspiro[5.5]undecane-9-carboxylate hydrochloride (1.38 mmol), 2-(isobutylcarbamoylamino)acetic acid (1.15 mmol), dimethylformamide (3.8 mL), triethylamine (1.72 mmol) and HATU (1.26 mmol. Stir at room temperature for 16 hours, then dilute with water (50 mL) and ethyl acetate (50 mL). Wash the organic phase with concentrated ammonium chloride (50 mL) and brine (50 mL). Dry the organics over sodium sulfate, filter, and concentrate under reduced pressure. Purify the intermediate by flash chromatography (40 g silica gel cartridge) eluting with 0-10% methanol in ethyl acetate to yield tert-butyl 9-[2-(isobutylcarbamoylamino)acetyl]-4,9-diazaspiro[5.5]undecane-4-carboxylate (0.38 g, 0.93 mmol): MS (m/z): 411.2 (M+H).

To a solution of tert-butyl 9-[2-(isobutylcarbamoylamino)acetyl]-4,9-diazaspiro[5.5]undecane-4-carboxylate (0.38 g, 0.93 mmol) in 1,4-dioxane (1.75 mL), add 4M HCl in 1,4-dioxane (8.77 mmol). Stir the reaction at room temperature for 5 hours, then concentrate under reduced pressure. Purify the residue by dissolving in methanol and loading into a SCX (ion exchange) column. Rinse the loaded column with methanol (3×25 mL) then flush the column with 2N ammonia in methanol. Combine and concentrate the ammonia washes to yield the title compound (0.25 g, 0.81 mmol): MS (m/z): 311.0 (M+H).

PREPARATION 10b

Alternative Preparation of 1-[2-(4,9-diazaspiro[5.5]undecan-9-yl)-2-oxo-ethyl]-3-isobutyl-urea Preparation of benzyl 2-(isobutylcarbamoylamino)acetate

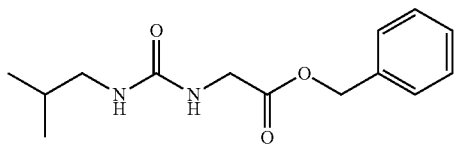 [SMILES: CC(C)CNC(=O)NCC(=O)OCc1ccccc1]

Charge 3-methylbutanoic acid (106.36 g), toluene (800 ml) and triethylamine (126.46 g) into a 3-neck flask (R1). Heat R1 to 90° C. Add a solution of DPPA (289.3 g) in toluene (400 ml) slowly (Care: N₂ released). Stir R1 at 90° C. for 30-60 mins, then cool to 20-30° C. In a separate flask (R2) charge benzyl 2-aminoacetate hydrochloride (200 g), triethylamine (150.54 g), and toluene (1000 ml) and stir at 20-30° C. for 1-2 hours. Add the R1 mixture into R2 drop wise slowly via addition funnel at 20-30° C. and stir for 1-2 hours. Slowly add the reaction mixture to water (2000 ml) with vigorous stirring. Separate the organic and extract the aqueous layer with EtOAc (2×1000 ml). Combine the organic layers and wash with 1 N hydrochloric acid (1000 ml), then 7% NaHCO₃ aq (1000 ml), then water (1000 ml), then 15% brine (1000 ml). Concentrate under reduced pressure. Slurry the residue with heptane (1000 ml) then filter the solid. Dry the filter cake under reduced pressure below 40° C. to give benzyl 2-(isobutylcarbamoylamino)acetate (218g; 98.1% assay; 81.5% yield).

Preparation of 2-(isobutylcarbamoylamino)acetic acid

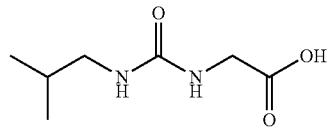

Charge benzyl 2-(isobutylcarbamoylamino)acetate (200 g; 98.1% assay), dry Pd/C (20 g; 10% w/w), and isopropyl alcohol (2000 ml) into an autoclave. Degas under vacuum and purge with hydrogen three times. Stir at 60° C. under 50-60 psi of H₂ for 4 hours. Cool the mixture to 20-30° C. and filter through diatomaceous earth and concentrate the filtrate under reduced pressure at 45-50° C. to 1-2Vol. Add acetonitrile (1000 ml) and concentrate under reduced pressure at 45-50° C. to 2-3 Vol. Cool the mixture to 5-10 C ° C. and filter. Dry the cake under reduced pressure at 45-50° C. to give of 2-(isobutylcarbamoylamino)acetic acid (112 g; 95.2% assay; 82.5% yield).

Preparation of Final Title Compound

To a round bottom flask add tert-butyl 4,9-diazaspiro[5.5]undecane-9-carboxylate hydrochloride (1.38 mmol), 2-(isobutylcarbamoylamino)acetic acid (1.15 mmol), dimethylformamide (3.8 mL), triethylamine (1.72 mmol), and HATU (1.26 mmol. Stir at room temperature for 16 hours, then dilute with water (50 mL) and ethyl acetate (50 mL). Wash the organic phase with concentrated ammonium chloride (50 mL) and brine (50 mL). Dry the organics over sodium sulfate, filter, and concentrate under reduced pressure. Purify the intermediate by flash chromatography (40 g silica gel cartridge) eluting with 0-10% methanol in ethyl acetate to yield tert-butyl 9-[2-(isobutylcarbamoylamino)acetyl]-4,9-diazaspiro[5.5]-undecane-4-carboxylate (0.38 g, 0.93 mmol): MS (m/z): 411.2 (M+H).

To a solution of tert-butyl 9-[2-(isobutylcarbamoylamino)acetyl]-4,9-diazaspiro[5.5]undecane-4-carboxylate (0.38 g, 0.93 mmol) in 1,4-dioxane (1.75 mL), add 4M HCl in 1,4-dioxane (8.77 mmol). Stir the reaction at room temperature for 5 hours, then concentrate under reduced pressure. Purify the residue by dissolving in methanol and loading into a SCX (ion exchange) column. Rinse the loaded column with methanol (3×25 mL) then flush the column with 2N ammonia in methanol. Combine and concentrate the ammonia washes to yield the final title compound, 1-[2-(4,9-diazaspiro[5.5]undecan-9-yl)-2-oxo-ethyl]-3-isobutyl-urea (0.25 g, 0.81 mmol): MS (m/z): 311.0 (M+H).

PREPARATION 10c

Alternative preparation of 1-[2-(4,9-diazaspiro[5.5]undecan-9-yl)-2-oxo-ethyl]-3-isobutyl-urea Preparation of O4-benzyl O9-tert-butyl 4,9-diazaspiro[5.5]undecane-4,9-dicarboxylate

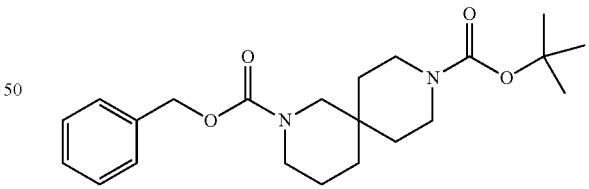

To a 20 L temperature controlled reactor charge tert-butyl 4,9-diazaspiro[5.5]undecane-9-carboxylate hydrochloride (2.06 moles; 600.00 g) followed by dichloromethane (6.00 L), then triethylamine (4.33 moles; 604 mL) is added. Set the jacket of the reactor to 0° C. When the temperature of the reaction mixture reaches 5° C., add benzyl chloroformate (2.10 moles; 311 mL) over about 20 minutes keeping the internal temperature below 20° C. When the addition is complete, warm the jacket to room temperature and stir the mixture overnight. Pour the reaction mixture into water (4 L) and separate the mixture. Concentrate the organics under reduced pressure to give the title compound (838 g; assumed 95.65% purity and 100% yield for the purposes of calculation in the next reaction) mass spectrum (m/z): 411.2 (M+23).

Preparation of benzyl 4,9-diazaspiro[5.5]undecane-4-carboxylate hydrochloride

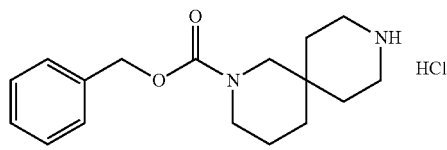 [SMILES: O=C(OCc1ccccc1)N1CCCC2(CCNCC2)C1 ; Cl]

To a 20 L temperature controlled reactor with jacket set at 0° C., add a solution of O4-benzyl O9-tert-butyl 4,9-diazaspiro[5.5]undecane-4,9-dicarboxylate (2.06 moles; 838.00 g; 95.65% purity) in 1,4-dioxane (19.63 moles; 1.68 L). When the temperature of the solution is 5° C., add hydrogen chloride (4 M in 1,4-dioxane; 10.32 moles; 2.58 L) at such a rate that the temperature does not rise above 20° C. When the addition is complete, warm the solution to room temperature and stir overnight. Concentrate the reaction mixture under reduced pressure to give a thick slurry. Add MTBE (3.35 L) and agitate the mixture for 30 minutes at 40° C. Allow the mixture to cool to room temperature and filter the precipitate. Wash the precipitate with MTBE (838 mL). Allow the precipitate to dry on the filter and then transfer to a vacuum oven for further drying to give the title compound (638 g; 95% yield) mass spectrum (m/z):289 [M(freebase)+1].

Preparation of benzyl 9-[2-(isobutylcarbamoylamino)acetyl]-4,9-diazaspro[5.5]undecane-4-carboxylate

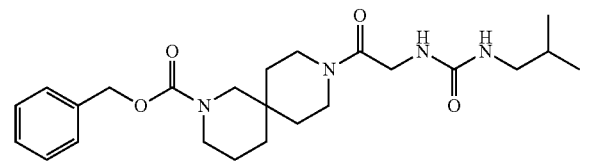 [SMILES: CC(C)CNC(=O)NCC(=O)N1CCC2(CCCN(C(=O)OCc3ccccc3)C2)CC1]

To 2-(isobutylcarbamoylamino)acetic acid (667.05 mmoles; 116.20 g) in dichloromethane (1.16 L) add 1,1'-carbonyldiimidazole (700.40 mmoles; 113.57 g) in portions. Stir the mixture at room temperature for 1 hour. Label this mixture A. In a separate vessel add benzyl 4,9-diazaspiro[5.5]undecane-4-carboxylate hydrochloride (700.40 mmoles; 413.68 g), dichloromethane (581 mL) and triethylamine (1.33 moles; 186 mL). Stir the mixture. Label this mixture B. Pour Mixture A into mixture B over 2 minutes. Stir the resulting mixture at room temperature. After 3 hours, add water (1000 mL). Separate the organic phase and concentrate under reduced pressure. Add ethyl acetate (581.00 mL) and agitate the mixture for 20 minutes at 40° C., then cool to room temperature then in ice for 20 minutes. Filter the precipitate and dry further in a vacuum oven to give the title compound. (137.1 g; 46.23% yield) mass spectrum (m/z): 445.2 (M+1). After allowing the filtrate to stand, a precipitate forms. Filter this precipitate and dry further in a vacuum oven to give the title compound. (9.30 g; 3.14% yield).

Preparation of Final Title Compound

Suspend benzyl 9-[2-(isobutylcarbamoylamino)acetyl]-2,9-diazaspiro[5.5]undecane-2-carboxylate (239.78 mmoles; 106.60 g) in ethanol (852.80 mL) and cyclohexene (1.20 moles; 121.90 mL), and add 5% palladium on charcoal (24 g; 55.4% moisture content). Heat the mixture to reflux and stir for 45 mins. Cool the mixture to room temperature, filter through a pad of diatomaceous earth washing the solid with ethanol, and concentrate under reduced pressure to give the final title compound, 1-[2-(4,9-diazaspiro[5.5]undecan-9-yl)-2-oxo-ethyl]-3-isobutyl-urea (79.2 g; 94% purity; 100% yield) mass spectrum (m/z):311.2 (M+1).

EXAMPLE 1a 1-isobutyl-3-[2-[4-[3-[4-[[4-methyl-1-[(2R,3R,4S,5S,6R)-3,4,5-trihydroxy-6-(hydroxymethyl)tetrahydropyran-2-yl]indol-3-yl]methyl]phenoxy]propyl]-4,9-diazaspiro[5.5]undecan-9-yl]-2-oxo-ethyl]urea

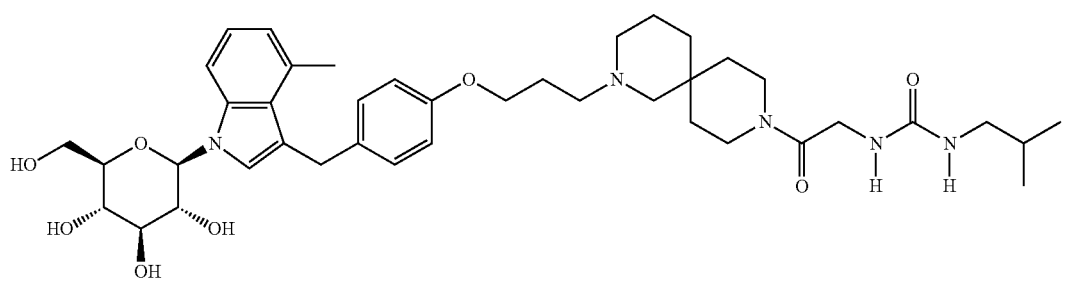 [SMILES: Cc1cccc2c1c(Cc1ccc(OCCCN3CCCC4(CCN(C(=O)CNC(=O)NCC(C)C)CC4)C3)cc1)cn2[C@@H]1O[C@H](CO)[C@@H](O)[C@H](O)[C@H]1O]

Scheme II, Step C: To a 0.25 L round bottom flask add [(2R,3R,4S,5R,6R)-3,4,5-triacetoxy-6-[4-methyl-3-[[4-(3-methylsulfonyloxypropoxy)phenyl]methyl]indol-1-yl]tetrahydropyran-2-yl]methyl acetate (7.2 g, crude), 1-[2-(4,9-diazaspiro[5.5]undecan-9-yl)-2-oxo-ethyl]-3-isobutyl-urea (12.28 mmol), acetonitrile (100 mL), and diisopropylethylamine (40.92 mmol). Heat at 80° C. for 16 hours then concentrate under reduced pressure. Add methanol (50 mL) and sodium methoxide (20.46 mmol, 30% solution in MeOH) and stir at room temperature for 1 hour. Quench by adding a small piece of dry ice. Concentrate under reduced pressure. Purify by reverse phase flash chromatography (400 g C18 cartridge) eluting with 5-80% water (0.1% formic acid) in acetonitrile (0.1 % formic acid) in three portions. Concentrate under reduced pressure to yield the title compound as a formic acid salt containing small impurities. Dissolve the salt in 7N ammonia in methanol (20 mL) then concentrate to form the free base. Purify the free base by flash chromatography (330 g silica gel cartridge) eluting with 5% 7N ammonia in methanol/dichloromethane. Concentrate the product fractions under reduced pressure to yield the title compound (1.75 g, 22.81%): MS (m/z): 746.6 (M+H). H$^1$ NMR (400.31 MHz, CD$_3$OD): δ 7.28 (d, J=8.4 Hz, 1H), 7.03 (d, J=8.4 Hz, 2H), 7.02 (s, 1H), 6.97 (t, J=8.8 Hz, 1H), 6.69 (d, J=7.2 Hz, 1H), 5.37 (d, J=9.2 Hz, 1H), 4.15 (s, 2H), 3.95 (t, J=6.0 Hz, 2H), 3.91 (d, J=1.6 Hz, 2H), 3.87-3.80 (m, 2H), 3.65 (dd, J=11.6, 5.6 Hz, 1H), 3.57-3.38 (m, 5H), 3.31 (bm, 2H), 2.90 (d, J=6.8 Hz, 2H), 2.46-2.13 (m, 8H), 1.88 (pentet, J=6.8 Hz, 2H), 1.68 (septet, J=6.8 Hz, 1H), 1.61-1.28 (m, 8H), 0.86 (d, J=6.8, 6H).

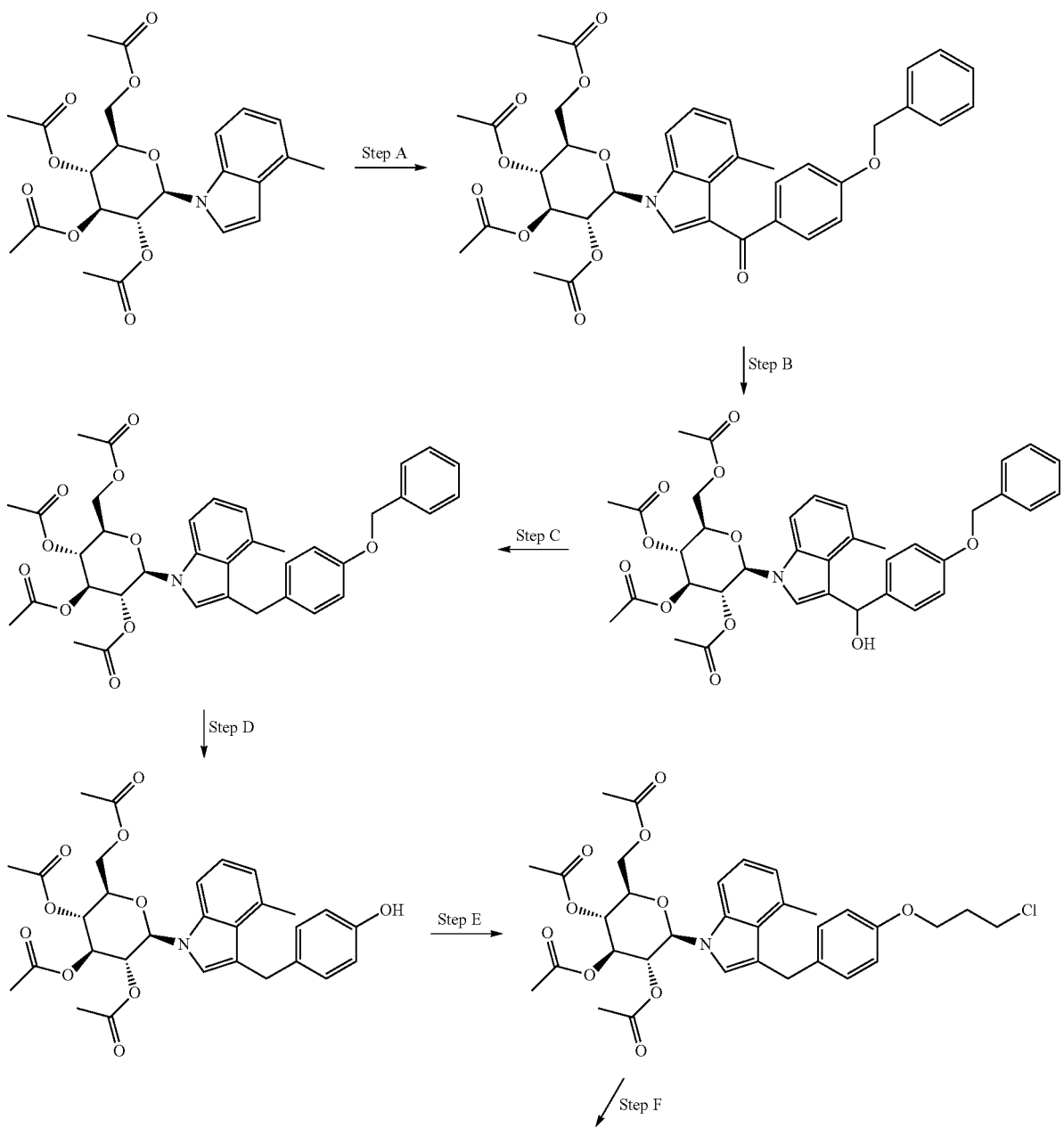

Scheme III

-continued

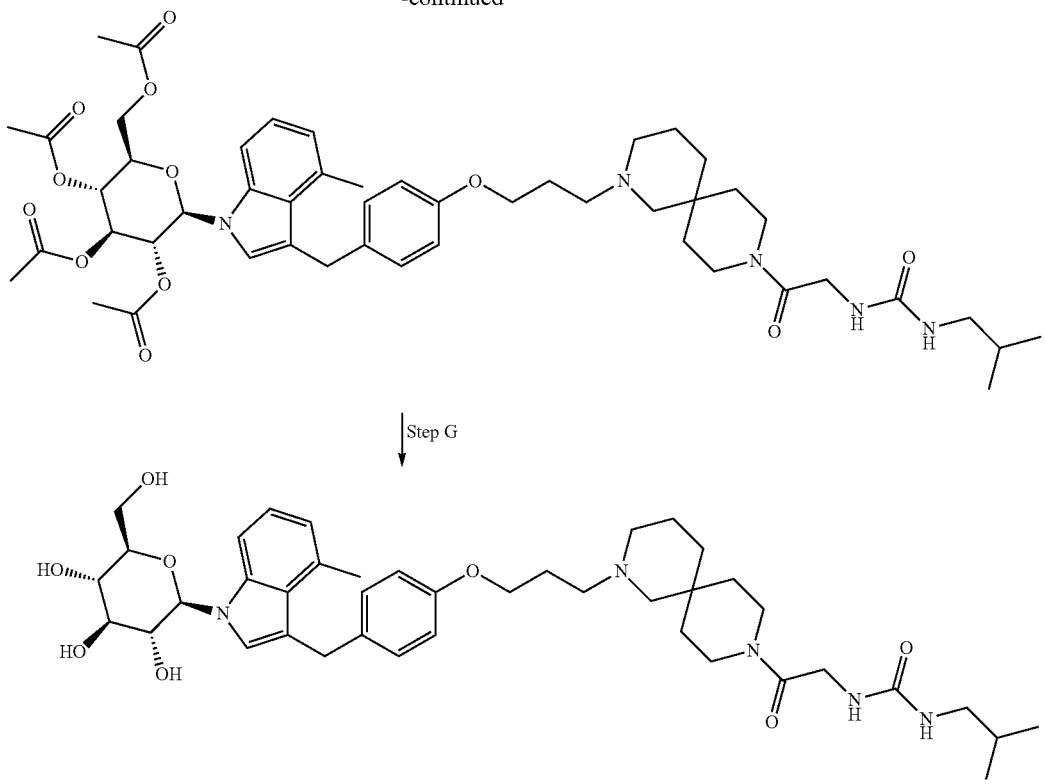

Formula I

PREPARATION 11

[2R,3R,4S,5R,6R)-3,4,5-triacetoxy-6-[3-(4-benzyloxybenzoyl)-4-methyl-indol-1-yl]tetrahydropyran-2-yl]methyl acetate

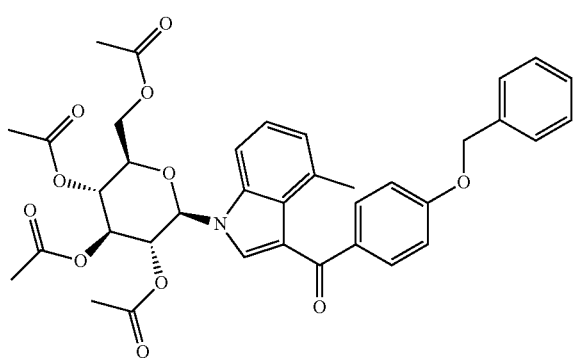 [SMILES: CC(=O)OC[C@H]1O[C@@H](n2cc(C(=O)c3ccc(OCc4ccccc4)cc3)c3c(C)cccc32)[C@H](OC(C)=O)[C@@H](OC(C)=O)[C@@H]1OC(C)=O]

Scheme III, Step A: To a 20 L temperature controlled reactor charge: dichloromethane (7.00 L), [(2R,3R,4S,5R,6R)-3,4,5-triacetoxy-6-(4-methylindol-1-yl)tetrahydropyran-2-yl]methyl acetate (1.52 moles; 700.00 g) and 4-benzyloxybenzoyl chloride (1.67 moles; 411.63 g). Set the reactor jacket to −30° C., allow the reactor contents to cool and add tin tetrachloride (1.97 moles; 513.74 g) over 30 mins maintaining internal temp between −5 and −10° C. When the addition is complete stir the mixture for 20 minutes at about −9° C. Pour the cold reaction mixture onto 20 L of crushed ice. Separate the organic layer, and extract the aqueous with dicholoromethane. Combine the organic extracts and concentrate under reduced pressure to about 2 L. Add 7 L MTBE and wash with hydrochloric acid (1M; 2×8 L) then water (8 L) then sodium hydrogen carbonate (saturated aqueous solution) then brine. Dry over MgSO$_4$, filter, and concentrate under reduced pressure to afford the title compound, which contains ~17% w/w MTBE (1377 g; assumed 74% purity and 100% yield for the purposes of calculation in the next reaction) mass spectrum (m/z): 672.2 (M+1).

PREPARATION 12

[(2R,3R,4S,5R,6R)-3,4,5-triacetoxy-6-[3-[(4-benzyloxyphenyl)-hydroxy-methyl]-4-methyl-indol-1-yl]tetrahydropyran-2-yl]methyl acetate

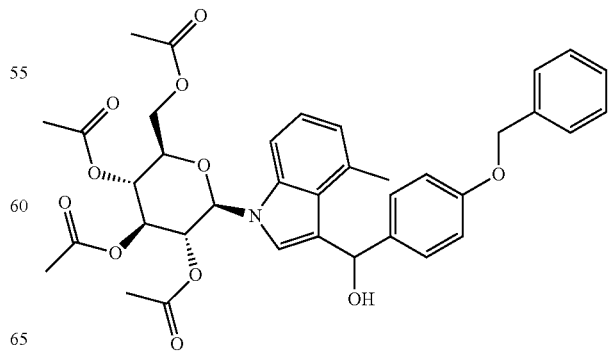

Scheme III, Step B: To a temperature controlled stirred reactor charge cerium (III) chloride heptahydrate (4.55 moles; 1.12 kg) in ethanol (4.96 L) and stir to give a solution. Add [(2R,3R,4S,5R,6R)-3,4,5-triacetoxy-6-[3-(4-benzyloxybenzoyl)-4-methyl-indol-1-yl]tetrahydropyran-2-yl] methyl acetate (1.52 moles; 1.38 kg) and tetrahydrofuran (7.57 L). Cool the mixture to +2° C. and add sodium tetrahydroborate (4.55 moles; 172.18 g) in portions over 3 hours maintaining the internal temperature between 0 and +5° C. during addition. When the addition is complete, stir the mixture at 5° C. for 1 hour. Add further sodium tetrahydroborate (687.24 mmoles; 26.00 g) and stir the mixture for 30 minutes. Add additional sodium tetrahydroborate (0.45 equiv; 687.24 mmoles; 26.00 g) and stir the mixture overnight. Pour the mixture into MTBE (5 L) and water (10 L). Slowly add hydrochloric acid (2 N) with stirring until mixture is slightly acidic to pH paper. Separate the organic layer, wash with brine, dry over MgSO4, filter, and concentrate under reduced pressure to afford the title compound in acceptable purity for use in the next step (1547 g; assumed 66% purity and 100% yield for the purposes of calculation in the next reaction) mass spectrum (m/z): 656.4 (M+1-18).

PREPARATION 13 of [(2R,3R,4S,5R,6R)-3,4,5-triacetoxy-6-[3-[(4-benzyloxyphenyl)methyl]-4-methyl-indol-1-yl]tetrahydropyran-2-yl]methyl acetate

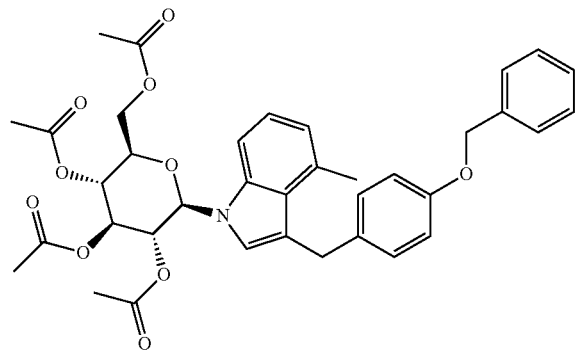 [SMILES: CC(=O)OC[C@H]1O[C@@H](n2cc(Cc3ccc(OCc4ccccc4)cc3)c3c(C)cccc32)[C@H](OC(C)=O)[C@@H](OC(C)=O)[C@@H]1OC(C)=O]

Scheme III, Step C: Cool a mixture of [(2R,3R,4S,5R,6R)-3,4,5-triacetoxy-6-[3-[(4-benzyloxyphenyl)-hydroxy-methyl]-4-methyl-indol-1-yl]tetrahydropyran-2-yl]methyl acetate (1.52 moles; 1.55 kg) in acetonitrile (6.19 L) and dichloromethane (6.19 L) in an brine/ice bath until the internal temperature is −5° C., then add triethylsilane (3.79 moles; 607 mL) over 2 minutes. Add boron trifluoride etherate (3.79 moles; 479 mL) dropwise maintaining the internal temperature below +5° C. Stir the mixture in the ice bath for 30 mins. Carefully add a mixture of NaHCO3 (saturated aqueous solution; 5 L) and water (4 L). Separate the organic phase and wash with water then brine then dry over MgSO4, filter, and concentrate under reduced pressure to afford a mixture of the title compound and compounds with one or more of the acetyl groups missing. Dissolve the residue in dichloromethane (1.86 L) and add acetic acid anhydride (7.58 moles; 716 mL) and N,N-dimethyl-4-pyridinamine, (75.78 mmoles; 9.26 g). Warm the mixture to 40° C. and gently agitate to aid dissolution then stir the mixture for 1 hour at room temperature. Concentrate the mixture under reduced pressure and slurry the residue in MTBE (6 L) overnight. Collect the solid by filtration and dry in an oven at 60° C. under reduced pressure to afford the title compound (692.8 g; 70% yield) mass spectrum (m/z): 658.3 (M+1) and 680.2 (M+23).

PREPARATION 14

[(2R,3R,4S,5R,6R)-3,4,5-triacetoxy-6-[3-[(4-hydroxyphenyl)methyl]-4-methyl-indol-1-yl]tetrahydropyran-2-yl]methyl acetate

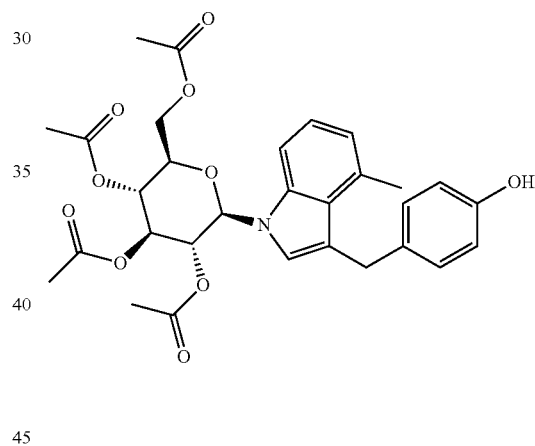

Scheme III, Step D: To a mixture of [(2R,3R,4S,5R,6R)-3,4,5-triacetoxy-6-[3-[(4-benzyloxyphenyl)methyl]-4-methyl-indol-1-yl]tetrahydropyran-2-yl]methyl acetate (1.00 equiv; 1.05 moles; 692.80 g), methanol (85.59 moles; 3.46 L; 2.74 kg), and tetrahydrofuran (42.57 moles; 3.46 L; 3.07 kg) add ammonium formate (5.27 moles; 332.10 g). Purge the reaction vessel with nitrogen and add 5% palladium on charcoal (69.30 g; Johnson Matthey type 87 L, 57.8% moisture content) as a slurry in isopropyl alcohol. Heat the mixture at 38-42° C. for 15 mins (moderate bubbling observed). Remove the heating bath and stir the reaction mixture for 15 minutes whilst cooling. Filter the mixture through diatomaceous earth and concentrate the filtrate under reduced pressure. Partition the residue between ethyl acetate (7.5 L) and water (1 L). Separate the organic layer and wash with brine then dry over MgSO4. Filter, and concentrate under reduced pressure to give the title compound (594 g; 99% yield) mass spectrum (m/z): 568.2 (M+1) and 590.2 (M+23).

PREPARATION 15

[(2R,3R,4S,5R,6R)-3,4,5-triacetoxy-6-[3-[[4-(3-chloropropoxy)phenyl]methyl]-4-methyl-indol-1-yl]tetrahydropyran-2-yl]methyl acetate

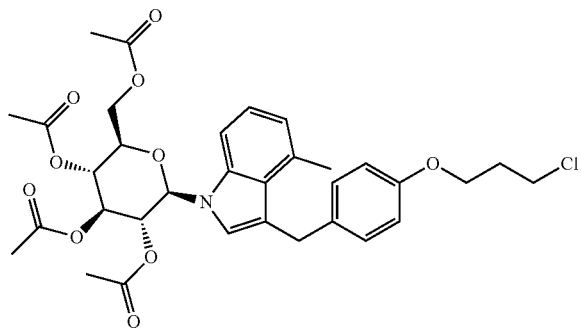 [SMILES: CC(=O)OC[C@H]1O[C@@H](n2cc(Cc3ccc(OCCCCl)cc3)c3c(C)cccc32)[C@H](OC(C)=O)[C@@H](OC(C)=O)[C@@H]1OC(C)=O]

Scheme III, Step E: To a mixture of [(2R,3R,4S,5R,6R)-3,4,5-triacetoxy-6-[3-[(4-hydroxyphenl)methyl]-4-methyl-indol-1-yl]tetrahydropyran-2-yl]methyl acetate (150.64 mmoles; 85.50 g) and acetonitrile (855.00 mL), add 1-bromo-3-chloro-propane, (180.76 mmoles; 17.88 mL) and potassium carbonate (301.27 mmoles; 41.64 g). Place the mixture under nitrogen and heat the mixture at a gentle reflux for 2 days. Add further 1-bromo-3-chloro-propane, (45.19 mmoles; 4.47 mL) and continue to heat the mixture overnight. Concentrate the mixture under reduced pressure and partition the residue between ethyl acetate and water. Separate the organic layer and wash with brine, dry over $MgSO_4$, filter, and concentrate under reduced pressure to give the title compound in sufficient purity for the next step. (124.4 g; assumed 78% purity and 100% yield for the purposes of calculation in the next reaction) mass spectrum (m/z): 644.2/646.2 (M+1).

PREPARATION 16

[(2R,3R,4S,5R,6R)-3,4,5-triacetoxy-6-[3-[[4-[3-[9-[2-(isobutylcarbamoylamino)acetyl]-4,9-diazaspiro[5.5]undecan-4-yl]propoxy]phenyl]methyl]-4-methyl-indol-1-yl]tetrahydropyran-2-yl]methyl acetate

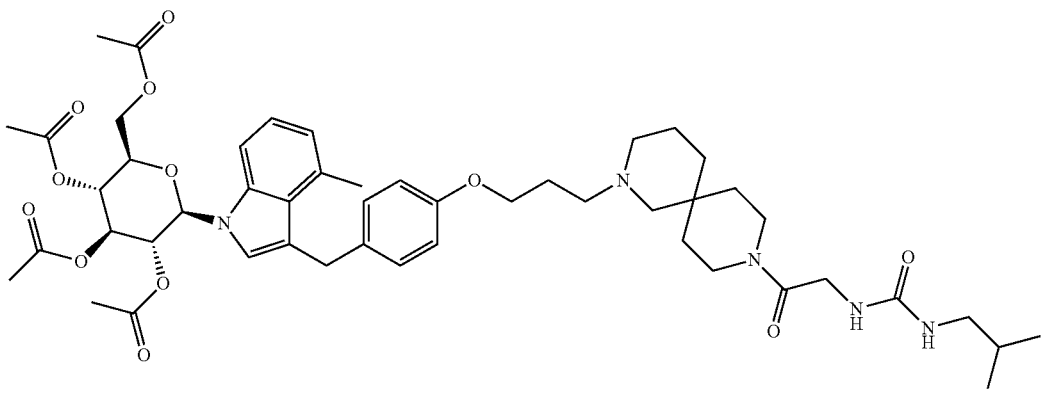 [SMILES: CC(=O)OC[C@H]1O[C@@H](n2cc(Cc3ccc(OCCCN4CCCC5(CCN(C(=O)CNC(=O)NCC(C)C)CC5)C4)cc3)c3c(C)cccc32)[C@H](OC(C)=O)[C@@H](OC(C)=O)[C@@H]1OC(C)=O]

Step III, Step F: To a stirred solution of [(2R,3R,4S,5R,6R)-3,4,5-triacetoxy-6-[3-[[4-(3-chloropropoxy)phenyl]methyl]-4-methyl-indol-1-yl]tetrahydropyran-2-yl]methyl acetate (143.38 mmoles; 118.40 g) in acetonitrile (829 mL) add 1-[2-(3,8-diazaspiro[5.5]undecan-3-yl)-2-oxo-ethyl]-3-isobutyl-urea (143.38 mmoles; 47.35 g), potassium carbonate (286.75 mmoles; 39.63 g), and potassium iodide (143.38 mmoles; 23.80 g). Heat the mixture at reflux under nitrogen overnight. Cool the reaction mixture to room temperature and add acetic acid anhydride (1.43 moles; 135.53 mL) and N,N-dimethyl-4-pyridinamine (14.34 mmoles; 1.75 g). Stir the mixture for 1 hour. Concentrate the mixture under reduced pressure and partition the residue between water and EtOAc. Separate the organic layer and wash with brine, dry over $MgSO_4$, filter, and concentrate under reduced pressure. The residue is combined with another lot prepared in a similar manner starting from [(2R,3R,4S,5R,6R)-3,4,5-triacetoxy-6-[3-[[4-(3-chloropropoxy)phenyl]methyl]-4-methyl-indol-1-yl]tetrahydropyran-2-yl]methyl acetate (6.2 mmol). Purify by flash column chromatography on silica gel (1.5 kg) eluting with 99:1 EtOAc:triethylamine (1cv), EtOAc (3cv's) and 190:10:1 EtOAc:MeOH:triethylamine (5cv's) to afford the title compound (68.2 g; 49% yield) mass spectrum (m/z): 918.6 (M+1).

EXAMPLE 1b

Alternative preparation of 1-isobutyl-3-[2-[4-[3-[4-[[4-methyl-1-[(2R,3R,4S,5S,6R)-3,4,5-trihydroxy-6-(hydroxymethyl)tetrahydropyran-2-yl]indol-3-yl]methyl]phenoxy]propyl]-4,9-diazaspiro[5.5]undecan-9-yl]-2-oxo-ethyl]urea

Sodium-Dependent Glucose Transporter 1 (SGLT1) and SGLT2 Assays

The cDNA encoding human SGLT1 (slc5a1, NM_000343) and mouse SGLT1 (slc5a1, NM_019810.4) are purchased from Openbiosystems, Invitrogen and Openbiosystems, respectively. The cDNA is cloned into pcDNA3.1+ for mammalian expression and is stably transfected into Chinese hamster ovary (CHO)-K1 cells using standard mammalian transfection procedures. An SGLT-expressing sub-clone of each over-expressing cell line is selected based on resistance to neomycin (Geneticin, Invitrogen) and activity in the $^{14}$C-α-methyl-D-glucopyranoside ($^{14}$C-AMG) uptake assay (see below). Stable SGLT-expressing cells are maintained using standard cell culture techniques.

The SGLT activity is measured as sodium-dependent $^{14}$C-AMG uptake in the above cell lines described as follows. One hundred μL of culture medium containing 30,000 cells are seeded to each well of a 96-well BioCoat poly-D-lysine plate (Becton Dickson) and cultured at 37° C. overnight. The culture medium is aspirated and cells are washed twice with 200 μL of Reaction Buffer (140 mM NaCl, 2 mM KCl, 1 mM $CaCl_2$, $MgCl_2$, and 14 mM N-2-hydroethylpiperrazine-N'-2-ethanesulfonic acid (Hepes), pH 7.5). The excess buffer is tapped out onto paper towels. Thirty-five μL of Reaction Buffer are added to each well. Five μL of a 10% dimethylsufoxide (DMSO) in Reaction Buffer containing varying concentrations of test compound or no compound as a control, is dispensed into the each well. The reaction is initiated by adding 10 μL of $^{14}$C-AMG in Reaction Buffer to make a final concentration of 4 μM. The plate is incubated at 37° C. for 125 minutes. The reaction is terminated by aspirating off Reaction Buffer and then washed three times with 200 μL of ice cold

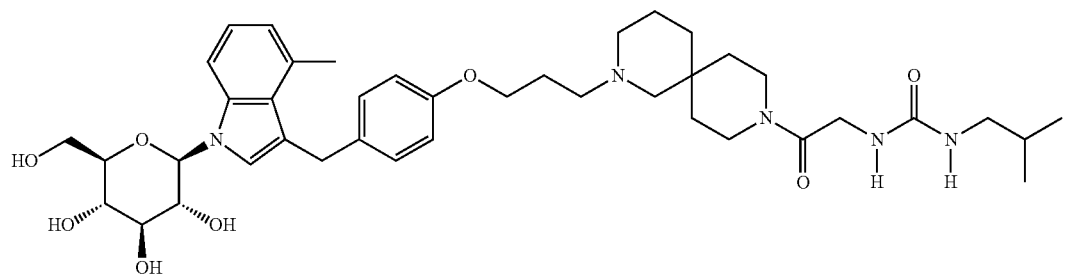 [SMILES: Cc1cccc2c1c(Cc1ccc(OCCCN3CCCC4(CCN(C(=O)CNC(=O)NCC(C)C)CC4)C3)cc1)cn2[C@@H]1O[C@H](CO)[C@@H](O)[C@H](O)[C@H]1O]

Scheme III, Step G: Cool a mixture of [(2R,3R,4S,5R,6R)-3,4,5-triacetoxy-6-[3-[[4-[3-[9-[2-(isobutylcarbamoylamino)acetyl]-4,9-diazaspiro[5.5]undecan-4-yl]propoxy]phenyl]methyl]-4-methyl-indol-1-yl]tetrahydropyran-2-yl]methyl acetate (74.28 mmoles; 68.20 g) and methanol (341.00 mL) in an ice-bath. Add sodium methoxide (111.43 mmoles; 6.02 g). Stir the mixture for 10 minutes. Pour the mixture into water (3.5 L), then filter the mixture. Wash the solid with water, dry on the sinter, and further dry in a vacuum oven at 60° C. to give the title compound (49.8 g, 89% yield) mass spectrum (m/z): 750.6 (M+1).

Reaction Buffer. Manual aspiration is applied to ensure the complete removal of Reaction Buffer. Ten μL of 0.1 N NaOH is added to each well and then 100 μL of Supermix scintillation cocktail (PerkinElmer) is added. After mixing, the scintillation signal in the plate is counted in a MicroBeta (PerkinElmer). A ten-dose response curve is fitted to an empirical four-parameter model using ActivityBase (ID Business Solution) to determine the inhibitor concentration at half-maximal inhibition ($IC_{50}$).

The compound of example 1 herein is tested essentially as described above and exhibits an $IC_{50}$ for human SGLT1 of 35.2±14.1 nM (n=5) and an $IC_{50}$ for mouse SGLT1 of 14.9±10.4 nM (n=5). These data demonstrate that the compound of example 1 inhibits human and mouse SGLT1 in vitro.

Glucose Lowering Effects in Oral Glucose Tolerance Test (OGTT)

The test compound is formulated by adding a vehicle of 1% hydroxyethylcellulose, 0.25% Tween® 80 w/antifoam 0.05% to preweighed test compound to make a 1 mg/ml solution. The mixture is probe sonicated for approximately 1 minute. A stir bar is added, and the resulting suspension is stirred continuously throughout dosing.

Two separate groups of single housed C57Bl/6 mice are used to demonstrate glucose lowering during OGTTs. The first set of mice receiving an OGTT 18 hours after compound administration, the second 8 hours after compound administration. The first set of animals are weighed and body weights used to determine study groups (n=5), within a working range of 26-30 g. After grouping, the mice are orally gavaged with 10 ml/kg of test compound preparation or vehicle, thirty seconds apart. The mice are then Both sets, 18 and 8 hour OGTT, of mice are then fasted overnight by removing access to food, late afternoon before test day. The following morning, the 8 hour OGTT mice are weighed and bled (via tail snip) for glucose. Study groups (n=5) are determine using fasted glucose values, within a working range of 80-100 mg/dl. After grouping the mice are orally gavaged with compound, thirty seconds apart. These mice then receive an OGTT 8 hours after compound administration.

At eight and eighteen hours after each respective compound treatment is started, a baseline blood sample is taken for measuring glucose (from the first animal). The animal is then immediately given an oral dose of 50% dextrose (Hospira®) at 3 g/kg. Blood samples are taken for glucose, exactly thirty seconds apart, by tail vein so that blood is collected in each animal at 20, 40, and 60 minutes after the dextrose dose.

As shown in table 1, the compound of example 1 delivers a decrease in the glucose excursion when an oral bolus of 50% dextrose (Hospira®) is given to a normal glycemic C57Bl/6 mouse eight or eighteen hours after administration. Example 1 also demonstrates a decrease in baseline adjusted glucose area under the curve (AUC) during both OGTTs. In addition, example 1 decreases the average maximum concentration of plasma glucose (Cmax) during the OGTTs while increasing the average time that it takes for glucose to reach maximum concentration (Tmax).

I claim:

1. A compound of the formula:

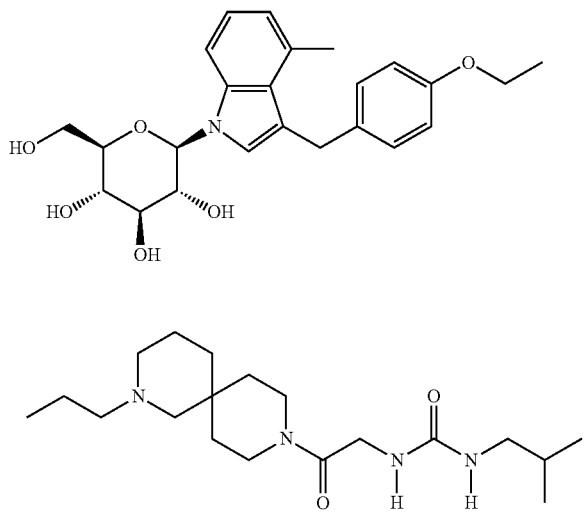

or a pharmaceutically acceptable salt thereof.

TABLE 2

Glucose lowering effects in OGTT.
Oral Glucose Tolerance Test Results Mean ± SEM
1 way ANOVA/Dunnett's compared to vehicle **p<0.01

|   | Vehicle @ 8 hrs post Dose | Example 1 10 mg/kg @ 8 hrs post Dose | Vehicle @ 18 hrs post Dose | Example 1 10 mg/kg @ 18 hrs post Dose |
|---|---|---|---|---|
|   | Glucose (mg/dl) | | | |
| 0 Minute | 83.3 ± 5.10 | 75.8 ± 2.48 | 79 ± 1.17 | 79.2 ± 4.51 |
| 20 Minute | 203.4 ± 23.3 | 114 ± 3.36** | 257.8 ± 19.1 | 121.4 ± 5.16** |
| 40 Minute | 168.5 ± 6.58 | 131 ± 6.81** | 202.8 ± 5.38 | 127 ± 9.78** |
| 60 Minute | 142.6 ± 5.58 | 125.8 ± 7.52 | 154.7 ± 5.32 | 125 ± 7.27** |
| Baseline Adjusted AUC | 4699 ± 602 | 2370 ± 315** | 6809 ± 419 | 2258 ± 252** |
| Glucose Cmax | 205.7 ± 22.2 | 132.9 ± 6.68** | 261.1 ± 16.3 | 134.2 ± 6.72** |
|   | Time (minutes) | | | |
| Glucose Tmax | 28 ± 4.9 | 44 ± 7.48 | 24 ± 4 | 44 ± 7.48 |

2. The compound according to claim 1 which is:

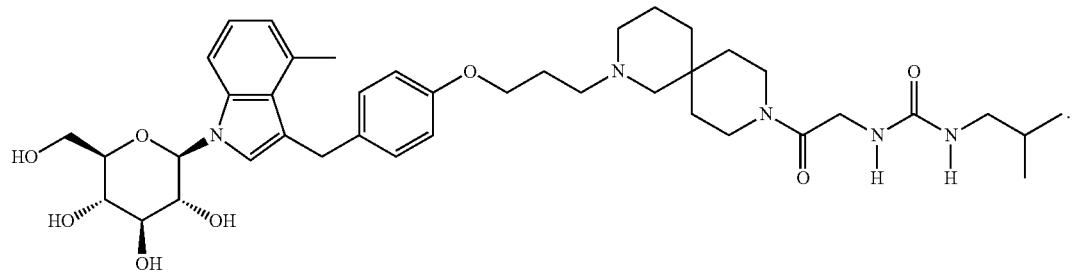 [SMILES: Cc1cccc2c1c(Cc1ccc(OCCCN3CCCC4(CCN(C(=O)CNC(=O)NCC(C)C)CC4)C3)cc1)cn2[C@@H]1O[C@H](CO)[C@@H](O)[C@H](O)[C@H]1O]

3. A method of treating diabetes in a patient comprising administering to a patient in need of such treatment an effective amount of a compound, or pharmaceutically acceptable salt thereof, according to claim 1.

4. A method of treating type 1 diabetes in a patient comprising administering to a patient in need of such treatment an effective amount of a compound, or pharmaceutically acceptable salt thereof, according to claim 1.

5. A method of treating type 2 diabetes in a patient comprising administering to a patient in need of such treatment an effective amount of a compound, or pharmaceutically acceptable salt thereof, according to claim 1.

6. A pharmaceutical composition comprising a compound or salt according to claim 1 with one or more pharmaceutically acceptable carriers, diluents, or excipients.

* * * * *